United States Patent [19]

Takemoto et al.

[11] 4,021,418

[45] May 3, 1977

[54] METHOD OF REMOVING FORMYL GROUPS FROM N-FORMYL-AMINO ACID AND N-FORMYL-PEPTIDE ESTERS

[75] Inventors: Tadashi Takemoto, Toyonaka; Fusayoshi Kakizaki, Kawasaki; Yasuo Ariyoshi; Ichiro Noda, both of Yokohama, all of Japan

[73] Assignee: Ajinomoto Co., Inc., Tokyo, Japan

[22] Filed: Nov. 26, 1975

[21] Appl. No.: 635,746

[30] Foreign Application Priority Data

Dec. 5, 1974 Japan .......................... 49-140646

[52] U.S. Cl. ..................... 260/112.5 R; 260/309.6; 260/313.1; 260/326.14 T; 260/468 J; 260/468 K; 260/471 R; 260/471 A; 260/481 R; 260/482 R; 260/482 P

[51] Int. Cl.² ................. C07G 7/00; C07C 103/52

[58] Field of Search ................. 260/112.5 R, 468 J, 260/468 K, 471 A, 471 R, 481 R, 482 R, 309.6, 313.1, 326.14 T

[56] References Cited

OTHER PUBLICATIONS

Geiger et al., Chem. Ber., 101, 3386–3391 (1968).

*Primary Examiner*—Lewis Gotts
*Assistant Examiner*—Reginald J. Suyat
*Attorney, Agent, or Firm*—Hans Berman

[57] ABSTRACT

The masking N-formyl group of an N-formyl-amino acid ester or N-formyl-peptide ester is removed without major side reactions when the ester is reacted in an inert liquid medium with hydroxylamine of which at least 70% is present in the form of a salt with a strong acid, the remainder, if any, being present as the free base or the salt of a weak acid.

10 Claims, No Drawings

METHOD OF REMOVING FORMYL GROUPS FROM N-FORMYL-AMINO ACID AND N-FORMYL-PEPTIDE ESTERS

This invention relates to the removal of masking groups from the nitrogen atoms of amino acid and peptide esters, and particularly to the removal of masking formyl groups from such esters.

While the amino groups of amino acid and peptide esters are readily masked by formyl groups, it was common practice heretofore to employ benzyloxycarbonyl and tert-butyloxycarbonyl groups for this purpose in the synthesis of peptides and similar reactions. The known masking groups require phosgene for their introduction, a dangerously toxic gas, but they have the advantage of being removed easily when no longer required. No practical method of removing formyl groups from the nitrogen atoms of amino acid esters or peptide esters was available prior to this invention.

Acid hydrolysis or alcholysis and catalytic hydrogenation are the conventional methods of removing formyl groups from amino groups and are effective, for example, in amino acids. These methods, however, when applied to esters of amino acids or peptides tend to remove the alcohol moiety from the ester and to break the peptide bond. It has also been known that hydrazine, hydroxylamine, and salts of hydroxylamine with weak acids can be used for removal of masking formyl groups from nitrogen atoms in organic compounds which are not esters (Lafrancier, Bull. Soc. Chim. France 1965, 36688; Geiger, Brit. Pat. No. 1182450), but these methods produce hydrazides and hydroxamic acids from masked amino acid esters, and hydroxylamine produces diketopiperazine from dipeptide esters when used in the known manner.

It has now been found that formyl groups can be removed from the amino groups of amino acid esters and peptide esters without major side reactions by means of hydroxylamine in an inert liquid reaction medium if at least 70% of the hydroxylamine is present in the medium as the salt of a strong acid, the latter term referring to acids having a first dissociation constant of not less than $1.0 \times 10^{-1}$ at 25° C. The remainder of the hydroxylamine, if any, may be present as the free base or as the salt of a weaker acid. The presence of at least 5% of the hydroxylamine as the free base or the weak acid salt may even improve the yield of the desired ester free from masking groups.

The strong acids suitable for forming hydroxylamine salts in the method of this invention include, but are not limited to, the conventional mineral acids, such as hydrochloric and sulfuric acid. Strong organic acids, such as monomethylsulfuric acid, benzenesulfonic acid, and trifluoroacetic acid are equally effective, but do not offer any advantages that would justify their higher cost. The free base is not stable in the presence of atmospheric oxygen and is conveniently produced in the reaction medium from the inexpensive hydrochloride or sulfate by means of an alkali metal hydroxide. The weak acid salts are similarly prepared most conveniently in the reaction medium from the mineral acid salts by means of sodium acetate, sodium propionate, and like inexpensive salts of alkali metals.

The method is generally applicable to all amino acid and peptide esters that are employed in peptide synthesis. The alcohol moiety of the ester has no significant bearing on the removal of the formyl group from a masked nitrogen atom. The esters of the lower alkanols having up to three carbon atoms and of benzyl alcohol are widely used in this art, and these alcohols provide typical although not necessary moieties for the esters which may serve as starting materials for the method of this invention. We are not aware of an amino acid or peptide ester of a primary or secondary alcohol that could not be stripped successfully of a masking formyl group by this method.

The reaction between the masked ester and hydroxylamine proceeds smoothly if the reactants are brought together in a liquid medium inert to them and to the desired reaction product. Temperature affects the reaction rate in the usual manner. If an optically active product is desired, the highest temperature which will not cause significant racemization is preferred for a short reaction time. The maximum yield is obtained at 70° C in 1 to 4 hours in most instances, while 5 to 12 hours may be needed at 50° C and 2 to 4 days at about 25° C.

At least an equimolecular amount of hydroxylamine is needed, based on the formyl groups in the ester, but an excess is usually beneficial, the practical range of hydroxylamine concentration being between 1.5 and 7 moles per mole of ester. An excess of less than 50% does not produce a significant increase in yield or reaction rate, and no further improvement is observed with more than 7 moles hydroxylamine, the best ratio of hydroxylamine to ester being the same whether the hydroxylamine is present entirely as a strong acid salt or partly as the free base or as a weak acid salt within the limit of 30%.

The amino group that is to be stripped of a masking formyl group according to this invention may be that of any amino acid ester or peptide ester, and the result is not affected by many other reactive moieties in the ester, such as a free carboxyl or amino group, an amide or thiol group. The invention has been found to be particularly useful in the synthesis of N-aspartyl amino acid esters which are known sweetening agents because it is not affected by the free carboxyl group of the aspartyl moiety.

The inert solvent medium may be chosen on the basis of cost so that water and the monohydric and polyhydric alcohols having up to four carbons are preferred. In addition to water and the low monoalkanols, glycerol and propyleneglycol, for example, and mixtures of these solvents may be employed. They are advantageous in that they dissolve the starting materials as well as the desired products.

Unless the reaction mixture is employed directly in a further reaction, the amino acid ester or peptide ester free from masking formyl groups may be recovered by methods conventional in themselves, as by lowering the temperature of the mixture, adding non-solvents miscible with the medium, partial evaporation of the medium, and the like.

The following examples are further illustrative of this invention. Percentage yields in these Examples are based on the amino acid or peptide esters having amino groups masked by formyl that were employed as starting materials. The products free from masking formyl groups were determined in the diluted reaction mixture by paper electrophoresis, staining of the chromatogram with ninhydrin-cadmium reagent [Z. Physiol. Chem. 309 (1957) 219], excision of the spot indicating the desired compound, elution with methanol, and measurement of absorbance of the eluate at 510 m$\mu$.

EXAMPLE 1

9.6 g N-Formyl-α-L-aspartyl-L-phenylalanine methyl ester (30 millimole) and 10.4 g hydroxylamine hydrochloride (150 millimole) were dissolved in 36 ml 90% methanol, and the solution was stirred three hours at 70° C. Analysis of an aliquot of the reaction mixture indicated a yield of 86%.

The bulk of the reaction mixture was evaporated, and the residue was dissolved in 40 ml 3 N hydrochloric acid. The solution was stored overnight in a refrigerator to precipitate crystals of α-L-aspartyl-L-phenylalanine methyl ester hydrochloride. The crystals were filtered off and weighed 8.5 g. When a solution of the crystals in 50 ml water was stored overnight in the refrigerator, it yielded a precipitate of 6.8 g free α-L-aspartyl-L-phenylalanine methyl ester (75% yield) having a melting point of 235° − 236° C. $[\alpha]_D^{20} = +32.2°$ (c = 1, acetic acid).

EXAMPLE 2

1.75 g N-Formyl-L-aspartic acid α-methyl ester (10 millimole) and 3.5 g hydroxylamine hydrochloride (50 millimole) were dissolved in 10 ml 90% methanol, and the solution was stirred at 70° C for 4 hours. The reaction mixture was then found to contain L-aspartic acid α-methyl ester in a yield of 85%.

EXAMPLE 3

2.07 g N-Formyl-L-phenylalanine methyl ester (10 millimole) and 3.5 g hydroxylamine hydrochloride (50 millimole) were dissolved in 12 ml methanol, and 0.82 g sodium acetate (10 millimole) was added to the solution to convert a part of the hydroxylamine hydrochloride to the acetate.

The solution was stirred 90 minutes at 70° C. It then contained L-phenylalanine methyl ester in a yield of 80%.

EXAMPLE 4

2.3 g N-Formyl-glycyl-L-leucine methyl ester (10 millimole) and 3.5 g hydroxylamine hydrochloride (50 millimole) were dissolved in 12 ml methanol, and 0.41 g sodium acetate (5 millimole) was added to the solution which was then held at 70° C for two hours.

It was found to contain glycyl-L-leucine methyl ester in a yield of 88%.

EXAMPLE 5

1.6 g N-Formyl-α-L-aspartyl-L-phenylalanine methyl ester (5 millimole) and 1.74 g hydroxylamine hydrochloride (25 millimole) were dissolved in 8 ml methanol, and the solution was stirred ten hours at 50° C. It then contained α-L-aspartyl-L-phenylalanine methyl ester in a yield of 83%.

EXAMPLE 6

1.7 g N-Formyl-α-L-aspartyl-L-phenylalanine ethyl ester (5 millimole) and 1.7 g hydroxylamine sulfate (10 millimole) were dissolved in 10 ml 75% isopropanol, and the solution was stirred 4 hours at 70° C. It then contained the α-L-aspartyl-L-phenylalanine ethyl ester in a yield of 74%.

EXAMPLE 7

1.8 g N-Formyl-α-L-aspartyl-L-tyrosine ethyl ester (5 millimole) and 1.4 g hydroxylamine hydrochloride (20 millimole) were dissolved in 8 ml 90% methanol, and the solution was stirred 3 hours at 70° C. It then contained α-L-aspartyl-L-tyrosine ethyl ester in a yield of 83%.

EXAMPLE 8

N-Formyl-L-aspartyl-L-phenylalanine methyl ester as prepared by condensing 1.4 g N-formyl-L-aspartic anhydride (10 millimole) with 1.8 g L-phenylalanine methyl ester (10 millimole) in 20 ml ethyl acetate. The reaction mixture was partly evaporated, and the residue was dissolved in a solution of 3.5 g hydroxylamine hydrochloride (50 millimole) in 30 ml methanol. A portion of the hydroxylamine hydrochloride was converted to the free base by the addition of 0.56 g (10 millimole) potassium hydroxide.

The mixture then was stirred at 70° C for 2 hours. It was thereafter found to contain α-L-aspartyl-L-phenylalanine methyl ester in a yield of 70%, and the β-isomer in a yield of 21% based on the N-formyl-L-aspartic anhydride employed as a starting material.

EXAMPLE 9

In a procedure similar to that of Example 5, 1.6 g N-formyl-α-L-aspartyl-L-phenylalanine methyl ester (5 millimole) and 1.74 g hydroxylamine hydrochloride (25 millimole) were dissolved in 10 ml methanol, and 2.05 g sodium acetate (25 millimole) was added to the solution to convert the entire hydroxylamine hydrochloride present to the acetate. The solution then was stirred at 70° C for 90 minutes, and an aliquot was analyzed by thin layer chromatography.

Neither the starting material nor the desired α-L-aspartyl-L-phenylalanine methyl ester could be detected in the chromatogram.

EXAMPLE 10

A solution of 1.6 g N-formyl-α-L-aspartyl-L-phenylalanine methyl ester and 1.74 g hydroxylamine hydrochloride in 10 ml methanol was mixed with 1.4 g (25 millimole) potassium hydroxide to convert the entire hydroxylamine salt present to the free base, and the mixture was stirred at 70° C for 90 minutes. Neither the starting material nor the desired product could be found in a thin layer chromatogram of the reaction mixture.

What is claimed is:

1. A method of removing the formyl group from the nitrogen atom of an N-formyl-amino acid ester or N-formyl-peptide ester which comprises reacting said ester with an at least equimolecular amount of hydroxylamine in an inert, liquid medium until the corresponding amino acid ester or peptide ester is formed, at least 70% of said hydroxylamine being present in said medium as the salt of a strong acid having a first dissociation constant of not less than $1.0 \times 10^{-1}$ at 25° C, the remainder of said hydroxylamine being present in said medium as the free base or as the salt of a weak acid having a first dissociation constant smaller than $1.0 \times 10^{-1}$ at 25° C.

2. A method as set forth in claim 1, wherein said strong acid is hydrochloric or sulfuric acid.

3. A method as set forth in claim 2, wherein said hydroxylamine is present in said medium substantially entirely as the salt of said strong acid.

4. A method as set forth in claim 1, wherein the alcohol moiety of said ester is alkyl having up to three carbon atoms or benzyl.

5. A method as set forth in claim 1, wherein said ester is an ester of a primary or secondary alcohol.

6. A method as set forth in claim 1, wherein said weak acid is acetic acid or propionic acid, and at least 5 percent of said hydroxylamine is present in said medium as the salt of said weak acid or as said free base.

7. A method as set forth in claim 1, wherein said inert, liquid medium essentially consists of at least one member of the group consisting of water and alcohols having up to four carbon atoms.

8. A method as set forth in claim 1, wherein the temperature of said medium is between 20° and 80° C during said reacting.

9. A method as set forth in claim 8, wherein each mole of said ester is reacted with 1.5 to 7 moles of said hydroxylamine.

10. A method as set forth in claim 1, which futther comprises recovering the formed amino acid ester or peptide ester.

* * * * *